(12) United States Patent
Itoh et al.

(10) Patent No.: US 8,979,265 B2
(45) Date of Patent: Mar. 17, 2015

(54) FUNDUS CAMERA

(75) Inventors: Hiroshi Itoh, Yokohama (JP); Hajime Nakajima, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 306 days.

(21) Appl. No.: 12/724,682

(22) Filed: Mar. 16, 2010

(65) Prior Publication Data
US 2010/0238402 A1  Sep. 23, 2010

(30) Foreign Application Priority Data
Mar. 19, 2009  (JP) ................................ 2009-068577

(51) Int. Cl.
*A61B 3/14* (2006.01)
*A61B 3/10* (2006.01)

(52) U.S. Cl.
CPC ...................... *A61B 3/14* (2013.01)
USPC ............ 351/206; 351/205; 351/213; 351/221

(58) Field of Classification Search
USPC ......... 351/205, 206, 208, 210, 211, 213, 214, 351/221; 396/18
See application file for complete search history.

(56) References Cited

U.S. PATENT DOCUMENTS

| | | | | |
|---|---|---|---|---|
| 5,287,129 A | * | 2/1994 | Sano et al. | 351/233 |
| 5,594,512 A | * | 1/1997 | Yoneda et al. | 351/206 |
| 6,456,787 B1 | * | 9/2002 | Matsumoto et al. | 396/18 |
| 2003/0071966 A1 | * | 4/2003 | Matsumoto | 351/206 |
| 2004/0189937 A1 | * | 9/2004 | Okinishi | 351/206 |

FOREIGN PATENT DOCUMENTS

JP  2000-300521 A  10/2000

OTHER PUBLICATIONS

U.S. Appl. No. 12/712084, filed Feb. 24, 2010.
U.S. Appl. No. 12/704415, filed Feb. 11, 2010.

* cited by examiner

*Primary Examiner* — Mahidere Sahle
(74) *Attorney, Agent, or Firm* — Carter, DeLuca, Farrell & Schmidt, LLP

(57) ABSTRACT

In a photographing optical system, an autofluorescence barrier filter having a characteristic of transmitting a light having an autofluorescence wavelength and a near-infrared wavelength, and a near-infrared light cut-off filter having a characteristic of transmitting the visible light and blocking the near-infrared light are disposed to be replaceable. In the case of observing a fundus, the fluorescence barrier filter is inserted into an optical path in an observation photographing optical system, so that observation can be performed by using a near-infrared illuminating light. In the case of autofluorescence photographing, the photographing can be performed without filter switching. In the case of color photographing, at the time of observation, the observation is performed using the fluorescence barrier filter, and at the time of photographing, the photographing can be performed using the replaced infrared light cut-off filter.

17 Claims, 6 Drawing Sheets

FUNDUS CAMERA

BACKGROUND OF THE INVENTION

1. Field of the Invention

The present invention relates to a fundus camera for performing observation using a near-infrared light and performing color photographing and fluorescence photographing such as fundus autofluorescence (FAF) photographing.

2. Description of the Related Art

As an example of the fundus camera for observing and photographing the fundus, there are a mydriatic fundus camera, in which a mydriatic agent is instilled into an eye, and a non-mydriatic fundus camera, in which a mydriatic agent is not instilled into an eye.

In general, the mydriatic fundus camera is mainly used by an ophthalmologist. The mydriatic fundus camera is suitable for taking a plurality of photographs by using various photographing techniques such as the color photographing, the fluorescence photographing, and the specialized filter photographing. On the other hand, the non-mydriatic fundus camera is mainly used for a group medical examination or by an internist. The non-mydriatic fundus camera is suitable for taking a single photograph. However, the ophthalmologist may also practice the medical examination without the instillation of the mydriatic agent, so that a burden on a person to be examined can be reduced. Therefore, the non-mydriatic photographing has been demanded.

Japanese Patent No. 2000-300521 discusses a non-mydriatic fundus camera capable of performing observation using a near-infrared light and performing color photographing and visible fluorescence (FA) photographing. In the fundus camera, a visible light cut-off filter is disposed in a fundus illumination system to be insertable/removable, and a visible light observing unit such as an optical finder, and two image capture units for a near-infrared observing, and for photographing a still image, are disposed in a photographing system.

When the FA photographing is performed by using the fundus camera discussed in Japanese Patent No. 2000-300521, until a fluorescent light appears, the visible light cut-off filter is disposed outside the optical path, and the observation is performed through the finder. When the fluorescent light appears, the visible light cut-off filter is inserted into the optical path to allow the near-infrared light to illuminate the eye to be examined. The fundus image is observed through an observation image capture unit capable of performing the observation of a moving image.

In addition, at the time of photographing, the optical path is switched by a flip-up mirror, so that the photographing is performed. In addition, it is important that the exciter filter and the barrier filter used for the visible fluorescence photographing have a characteristic of transmitting the near-infrared light.

In addition, recently, the autofluorescence photographing has attracted attention as a new method of diagnosis for age-related macular degeneration (AMD). The autofluorescence was used for a laser scan opthalmoscopic apparatus in the early stage, but the autofluorescence has also been used for the fundus camera in these days.

When the autofluorescence photographing is performed by using the fundus camera, an exciter filter is inserted into a fundus illumination system, and an examiner performs the observation of the fundus of the eye to be examined and alignment by using a visible light. In addition, at the time of fluorescence photographing, a barrier filter is inserted into a photographing system in synchronization with the photographing, and the photographing is performed.

Conventionally, similar to a first conventional fundus camera illustrated in FIG. 4, in the mydriatic fundus camera capable of performing the autofluorescence photographing, to perform the color photographing and the autofluorescence photographing, the filter needs to be switched. In addition, as illustrated in FIG. 4, an illumination optical system L1 and an observation photographing optical system L2 are disposed. In the illumination optical system L1, for example, a halogen light source 1 is used as an observation light source, and a xenon tube 2 is used as a photographing light source. The halogen light source 1 and the xenon tube 2 emit a light having wavelengths of a visible light and a near-infrared light.

When the autofluorescence photographing is performed, in the optical path of the illumination optical system L1, as an illumination system 1, an exciter filter 3 for transmitting only the excited light and a planar plate 4 for correcting an optical path length inserted at the time of color photographing are disposed to be insertable/removable.

In addition, in the observation photographing optical system L2, as a photographing system 1, a barrier filter 5, which is inserted at the time of fluorescence photographing and transmits only a light in a fluorescence wavelength band of the autofluorescence, and a near-infrared cut-off filter 6, which is inserted at the time of color photographing are disposed to be insertable/removable. The near-infrared cut-off filter 6 is used to prevent good image quality from deteriorating due to an excessive increase in red component of the color-photographed image.

In the aforementioned fundus camera, at the time of observation in the autofluorescence photographing mode, the exciter filter 3 needs to be inserted into the illumination system 1, the near-infrared cut-off filter 6 needs to be inserted into the photographing system 1, and the alignment and observation need to be performed through the finder. In addition, at the time of photographing, in the photographing system 1, the near-infrared cut-off filter 6 is replaced with the barrier filter 5, so that the photographing is performed.

In addition, at the time of observation and photographing in the color photographing mode, the planar plate 4 is inserted into the illumination system 1, and the near-infrared cut-off filter 6 is inserted into the photographing system 1. In addition, in the fundus camera, since the observation is performed by using the visible light, a mydriatic agent needs to be instilled into the eye of a person to be examined to obtain mydriasis.

In a second conventional fundus camera illustrated in FIG. 5, in the illumination optical system L1, a near-infrared light source 11 that emits a near-infrared light is used as an observation light source, and a xenon tube 12 that emits a light having wavelengths of a visible light and a near-infrared light is used as a photographing light source.

In the illumination optical system L1, as an illumination system 1, the near-infrared light cut-off filter 13 and the exciter filter 14 that transmits also the near-infrared light are disposed to be replaceable, and as an illumination system 2, the near-infrared light cut-off filter 15 and the planar plate 16 are disposed to be insertable/removable. In the observation photographing optical system L2, as a photographing system 1, in front of the image capture unit 17, the barrier filter 18 and the planar plate 19 are disposed to be replaceable. Therefore, the photographing in the color photographing mode and the fluorescence photographing mode can be performed.

As illustrated in FIG. 5, if one image capture unit is used, the image capture unit 17 needs to be configured to perform the observation by using the near-infrared light. At the time of still image photographing according to the second conventional fundus camera illustrated in FIG. 5, the infrared light cut-off filter needs to be inserted to the illumination optical system L1 or the observation photographing optical system L2.

Therefore, at the time of observation in the color photographing mode, the exciter filter 14 is inserted into the illumination system 1, the planar plate 16 is inserted into the illumination system 2, and the planar plate 19 is inserted into the photographing system 1, so that the observation is performed. In addition, at the time of photographing in the color photographing mode, the near-infrared light cut-off filter 13 is inserted into the illumination system 1, the planar plate 16 is inserted into the illumination system 2, and the planar plate 19 is inserted into the photographing system 1, so that the photographing is performed.

At the time of observation in the fluorescence photographing mode, the exciter filter 14 is inserted into the illumination system 1, the planar plate 16 is inserted into the illumination system 2, and the barrier filter 18 is inserted into the photographing system 1, so that the observation is performed. In addition, at the time of photographing in the fluorescence photographing mode, the exciter filter 14 is inserted into the illumination system 1, the near-infrared light cut-off filter 15 is inserted into the illumination system 2, and the barrier filter 18 is inserted into the photographing system 1, so that the photographing is performed.

As described above, to perform the photographing in the color photographing mode and the fluorescence photographing mode, three filter switching mechanisms are needed. The reason why the three switching mechanisms are needed is that, since the exciter filter 14 also transmits the infrared wavelength, the near-infrared light cut-off filters 13 and 15 for blocking the transmission of the infrared wavelength light are needed.

In a third conventional fundus camera illustrated in FIG. 6, two image capture units are provided to perform the color photographing and the autofluorescence photographing, and an illumination optical system L1 and observation photographing optical systems L2 and L3 are disposed. In the illumination optical system L1, for example, a halogen light source 21 is used as an observation light source, and a xenon tube 22 is used as a photographing light source. The halogen light source 21 and the xenon tube 22 emit a light having wavelengths of a visible light and a near-infrared light.

When the autofluorescence photographing is performed, in the optical path of the illumination optical system 1, as an illumination system 1, a exciter filter 23 for transmitting only the excited light and a planar plate 24 for correcting an optical path length inserted at the time of color photographing are disposed to be insertable.

In addition, in the observation photographing optical system L2, as a photographing system 1 a barrier filter 25, which is inserted at the time of fluorescence photographing and transmits only a light in a fluorescence wavelength band of the autofluorescence, and a planar plate 26, which is inserted at the time of color photographing and corrects an optical path length, are disposed to be insertable/removable. In addition, as a photographing system 2, a near-infrared light cut-off filter 28, which is needed to prevent good image quality from deteriorating due to an excessive increase in red component of the captured image, is disposed in front of a color-photographing image capture unit 27 of the observation photographing optical system L2. In an observation photographing optical system L3, which is branched by a switching mirror 29, an autofluorescence photographing image capture unit 30 is disposed.

In the fundus camera described above, at the time of observation in the autofluorescence photographing mode, a exciter filter 23 is inserted into the illumination system 1, a planar plate 26 is inserted into the photographing system 1, and alignment and observation are performed through a finder (not illustrated). In addition, at the time of photographing, in the photographing system 1, the planar plate 26 is replaced with the barrier filter 25, and the switching mirror 29 is inserted into the optical path, so that the photographing is performed by the image capture unit 30. In addition, at the time of observation and photographing in the color photographing mode, the planar plate 24 is inserted into the illumination system 1, and the switching mirror 29 recedes from the optical path, so that the photographing is performed by the image capture unit 27.

In addition, in the fundus camera described above, since the observation is performed by using the visible light, a mydriatic agent needs to be instilled into the eye of a person to be examined to obtain mydriasis.

The following Table 2 lists the examples of the conventional fundus cameras. In the Table, the symbol "NO" denotes that no filter exists at the corresponding position.

TABLE 2

| First conventional fundus camera |
|---|
| (1) Photographing Mode --- Color/Autofluorescence |
| (2) Observation Wavelength ---Visible Light |
| (3) Color --- Fluorescence |
| (4) Illumination System 1 Observation Time --- Planar Plate/Exciter |
| (5) Illumination System 1 Photographing Time --- Planar Plate/Exciter |
| (6) Illumination System 2 Observation Time --- NO/NO |
| (7) Illumination System 2 Photographing Time --- NO/NO |
| (8) Photographing System 1 Observation Time --- Near-Infrared Light Cut/Near-Infrared Light Cut |
| (9) Photographing System 1 Photographing Time --- Near-Infrared Light Cut/Barrier |
| (10) Photographing System 2 Observation Time --- NO/NO Photographing System 2 Photographing Time --- NO/NO |
| Second conventional fundus camera |
| (1) Photographing Mode --- Color/Visible Fluorescence |
| (2) Observation Wavelength --- Near-Infrared Light |
| (3) Color --- Fluorescence |
| (4) Illumination System 1 Observation Time --- Exciter/Exciter |
| (5) Illumination System 1 Photographing Time --- Near-Infrared Light Cut/Exciter |
| (6) Illumination System 2 Observation Time --- Planar Plate/Planar Plate |
| (7) Illumination System 2 Photographing Time --- Planar Plate/Near-Infrared Light Cut |
| (8) Photographing System 1 Observation Time --- Planar Plate/Barrier |
| (9) Photographing System 1 Photographing Time --- Planar Plate/Barrier |
| (10) Photographing System 2 Observation Time --- NO/NO Photographing System 2 Photographing Time --- NO/NO |
| Third conventional fundus camera |
| (1) Photographing Mode --- Color/Autofluorescence |
| (2) Observation Wavelength --- Visible Light |
| (3) Color --- Fluorescence |
| (4) Illumination System 1 Observation Time --- Planar Plate/Exciter |
| (5) Illumination System 1 Photographing Time --- Planar Plate/Exciter |
| (6) Illumination System 2 Observation Time --- NO/NO |
| (7) Illumination System 2 Photographing Time --- NO/NO |
| (8) Photographing System 1 Observation Time --- Planar Plate/Planar Plate |
| (9) Photographing System 1 Photographing Time --- Planar Plate/Barrier |

TABLE 2-continued

(10) Photographing System 2 Observation Time --- Near-Infrared Light Cut/Near-Infrared Light Cut
(11) Photographing System 2 Photographing Time --- Near-Infrared Light Cut --- Near-Infrared Light Cut In this manner, in the first and third conventional fundus cameras where the autofluorescence photographing can be performed, since the mydriatic fundus camera is basically used, the observation is performed by using the visible light. Therefore, a person to be examined needs to be subjected to mydriasis. In addition, in the second conventional fundus camera, since the observation is performed by using the near-infrared light, three filter switching mechanisms are needed for the apparatus for performing the fluorescence photographing and the color photographing.

SUMMARY OF THE INVENTION

The present invention is directed to a fundus camera capable of reducing the number of filter switching units, and performing color photographing and autofluorescence photographing in a non-mydriatic manner, thereby reducing a burden on a patient. Particularly, the present invention is directed to a fundus camera capable of screening a disease such as an age-related macular degeneration by using the autofluorescence photographing.

According to an aspect of the present invention, a fundus camera includes an illumination unit including a unit configured to illuminate a fundus of an eye to be examined with only a non-visible light to perform observation using the non-visible light and a unit configured to illuminate the fundus with a visible wavelength band and a non-visible light to perform photographing using the visible light, a fluorescence exciter filter disposed to be insertable/removable in/from an optical path between the illumination unit and the eye to be examined and configured to transmit only a light in the fluorescence wavelength band, a first driving unit configured to drive insertion and removal of the fluorescence exciter filter, an observation photographing optical system configured to receive a reflected light from the illuminated fundus and perform imaging of the fundus image, an image capture unit having a sensitivity to a near-infrared wavelength band and a visible wavelength band and configured to perform moving image capturing and still image capturing, a second driving unit configured to drive replacement between a fluorescence barrier filter and an infrared light cut-off filter, which have a characteristic of transmitting a light in the fluorescence wavelength band and a light in the near-infrared wavelength band, in an optical path of the observation photographing optical system, a photographing switch configured to perform the still image photographing, a photographing mode selection unit configured to switch a plurality of photographing modes, and a control unit configured to control a system based on an output of the photographing mode selection unit and an output of the photographing switch, wherein, at the time of observation, the control unit controls the fluorescence exciter filter to recede from the optical path using the first driving unit and controls the fluorescence barrier filter to be inserted into the optical path using the second driving unit, and wherein, at the time of color photographing, the control unit controls the fluorescence exciter filter to recede from the optical path using the first driving unit and controls the infrared light cut-off filter to be inserted into the optical path using the second driving unit, and wherein, at the time of fluorescence photographing, the control unit controls the fluorescence exciter filter to be inserted into the optical path through the first driving unit and controls the fluorescence barrier filter to be inserted into the optical path using the second driving unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
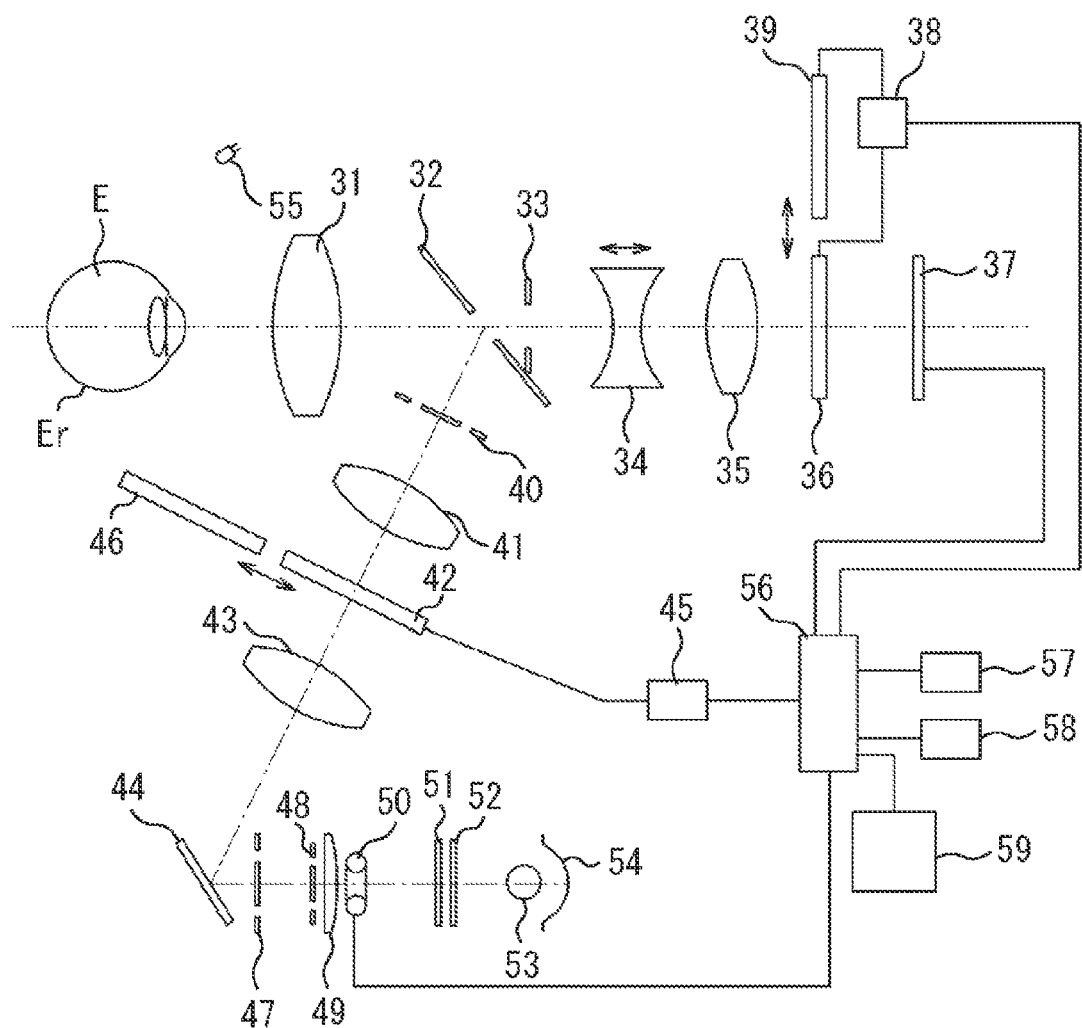
FIG. 1 illustrates a configuration of a fundus camera according to an exemplary embodiment of the present invention.

The exemplary embodiments of the present invention are described in detail with reference to FIGS. 1 to 3 below. FIG. 1 illustrates a configuration of a non-mydriatic fundus camera according to an exemplary embodiment. An observation photographing optical system is configured by sequentially arranging an objective lens 31, a perforated mirror 32, a photographing diaphragm 33, a focus lens 34, an imaging lens 35, an autofluorescence barrier filter 36, and an image capture unit 37 in front of an eye E to be examined. In addition, the autofluorescence barrier filter 36 is configured to be insertable/removable into/from an optical path and replaceable with a near-infrared light cut-off filter 39 by a first driving unit 38.

In the reflecting direction of the perforated mirror 32, a cornea diaphragm 40 having a ring-shaped aperture portion, a relay lens 41, an optical path length correction glass 42, a relay lens 43, and a mirror 44 are sequentially disposed. In addition, the optical path length correction glass 42 can be replaced with an autofluorescence exciter filter 46 by a second driving unit 45.

In the reflecting direction of the mirror 44, an eye-lens diaphragm 47 having a ring-shaped aperture portion for separating an illuminating light flux and a photographing light flux is disposed so that a reflected light, which is an unfavorable light from the eye lens of the eye E to be examined due to the illuminating light flux, is not incident to the photographing diaphragm 33. In addition, in the rear portion of the eye-lens diaphragm 47, a pupil diaphragm 48 having a ring-shaped aperture portion at a substantially conjugated position to the position of the pupil of the eye E to be examined, a lens 49, and a xenon tube 50, which is a photographing light source for illumination of a flash of a visible light are disposed.

In addition, in the rear portion of the xenon tube 50, a diffusing plate 51, a visible light cut-off filter 52, which does not transmit the visible light, and a halogen lamp 53, which is an observation illuminating light source are disposed, and in the rear portion of the halogen lamp 53, a reflecting mirror 54 is disposed, so that an illumination optical system is configured. In addition, in front of the eye E to be examined, an external fixation target 55 for guiding the eye E to be examined is disposed.

An output of the image capture unit 37 is connected to a control unit 56 that controls an entire system. Further, the output of the photographing mode selection unit 57 for selecting a plurality of photographing modes, and the output of the photographing switch 58 to be used for photographing a still image are connected to the control unit 56. In addition, the output of the control unit 56 is connected to the first driving unit 38, the second driving unit 45, the xenon tube 50, and a monitor 59 for displaying a captured moving image or still image of a fundus image.

Figure 2A:
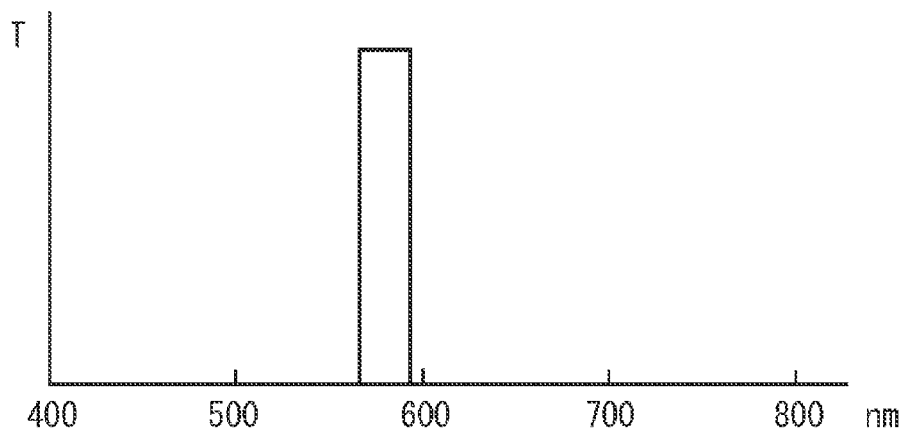
FIGS. 2A to 2C are graphs illustrating spectral characteristics of filters.

FIG. 2A is a graph illustrating a spectral characteristic of the autofluorescence exciter filter 46. The autofluorescence exciter filter 46 has a characteristic of transmitting a light in a fluorescence wavelength band of about 580 nm and blocking transmission of a light outside the wavelength band.

Figure 2B:
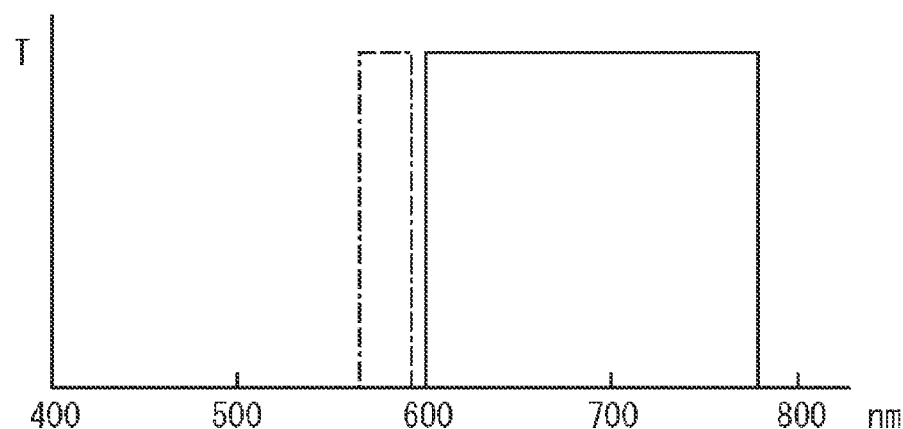

FIG. 2B is a graph illustrating a spectral characteristic of the autofluorescence barrier filter 36. The autofluorescence barrier filter 36 has a characteristic of transmitting a light in a wavelength band of at least 600 to 780 nm and blocking transmission of a light having a wavelength of less than 600 nm. The dotted line in FIG. 2B indicates the spectral characteristic of the autofluorescence exciter filter 46 illustrated in FIG. 2A. As illustrated in the FIG. 2B, there is no overlap in the transmission bands between the autofluorescence barrier filter 36 and the autofluorescence exciter filter 46.

Figure 2C:
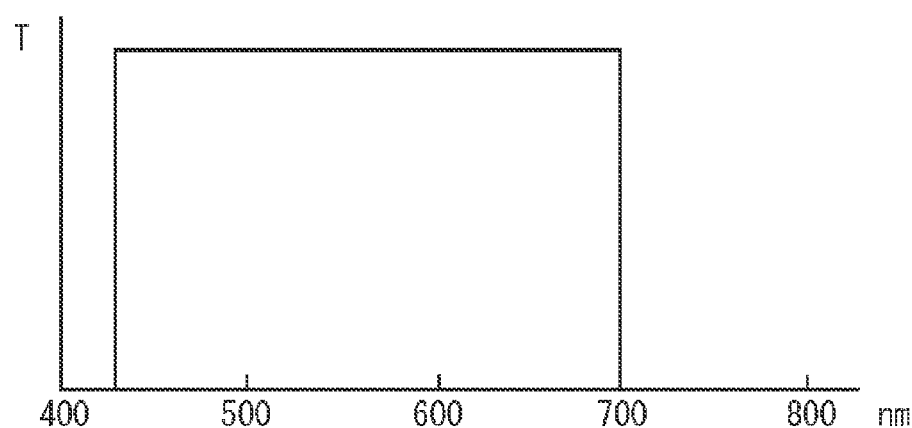

FIG. 2C is a graph illustrating a spectral characteristic of the near-infrared light cut-off filter 39. The near-infrared light cut-off filter 39 has a characteristic of transmitting a light in a wavelength band of 430 to 700 nm and blocking transmission of a light having a wavelength of more than 700 nm. This is because the color-photographed image does not deteriorate due to the transmission of the near-infrared light that is not a visible light.

Figure 3:
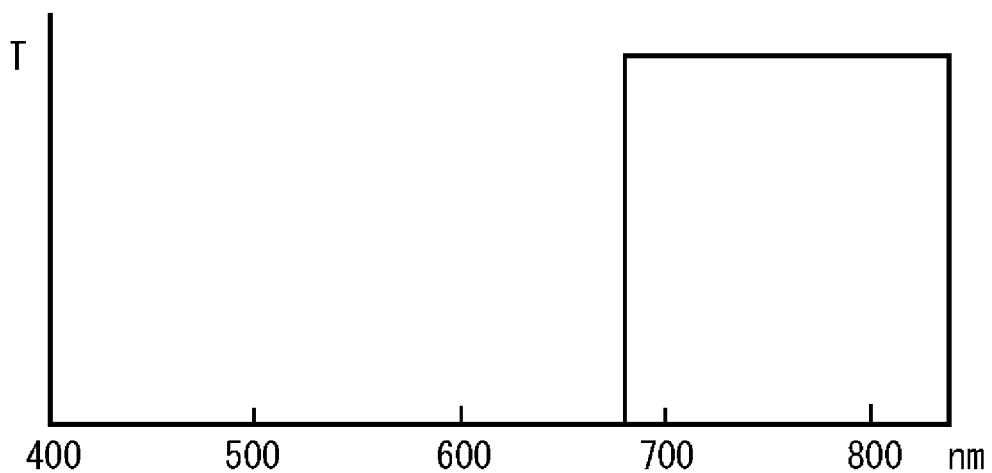
FIG. 3 is a graph illustrating a spectral characteristic of a filter.
Figure 4:
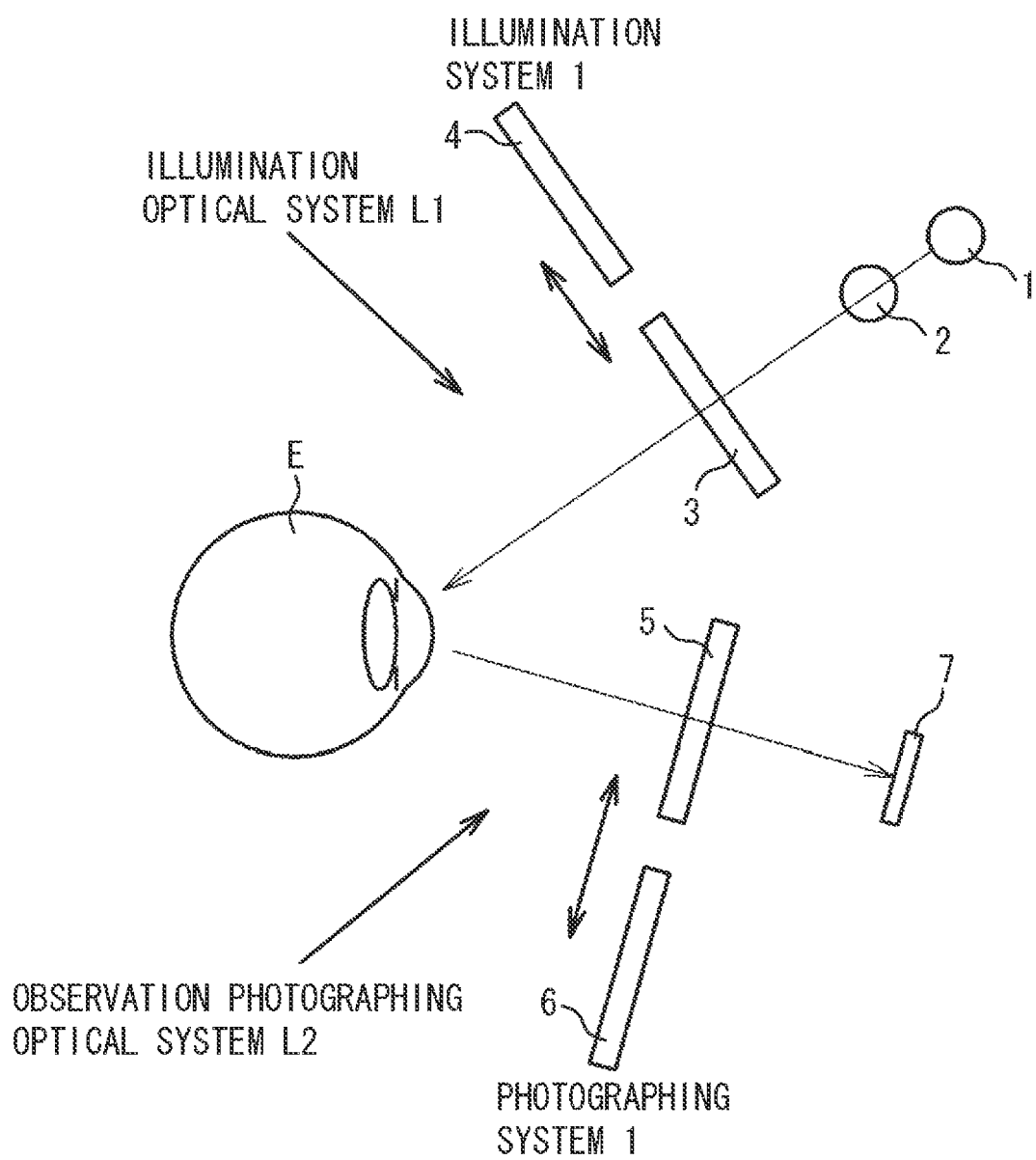
FIG. 4 illustrates a fundus camera according to a first conventional fundus camera.
Figure 5:
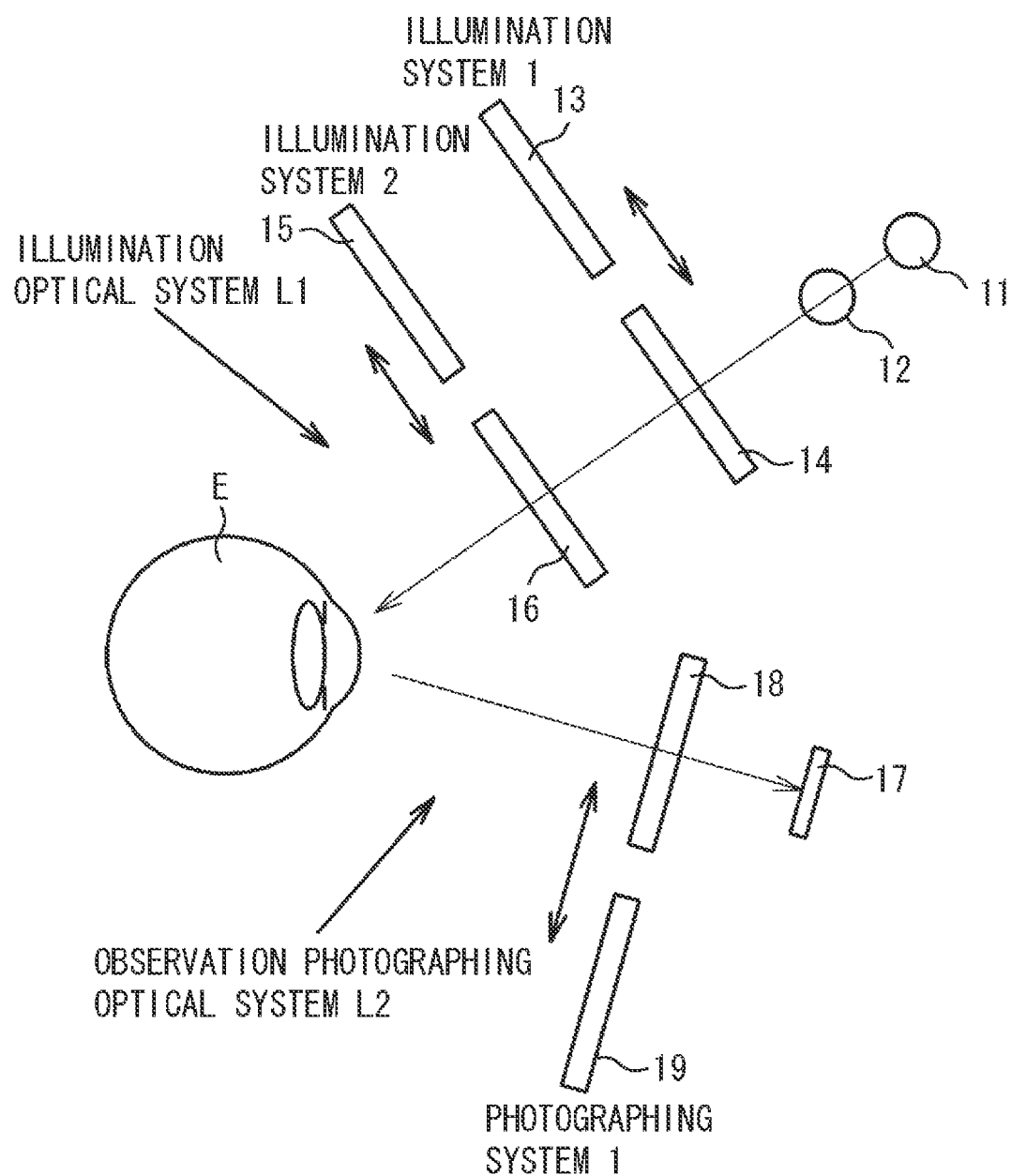
FIG. 5 illustrates a fundus camera according to a second conventional fundus camera.
Figure 6:
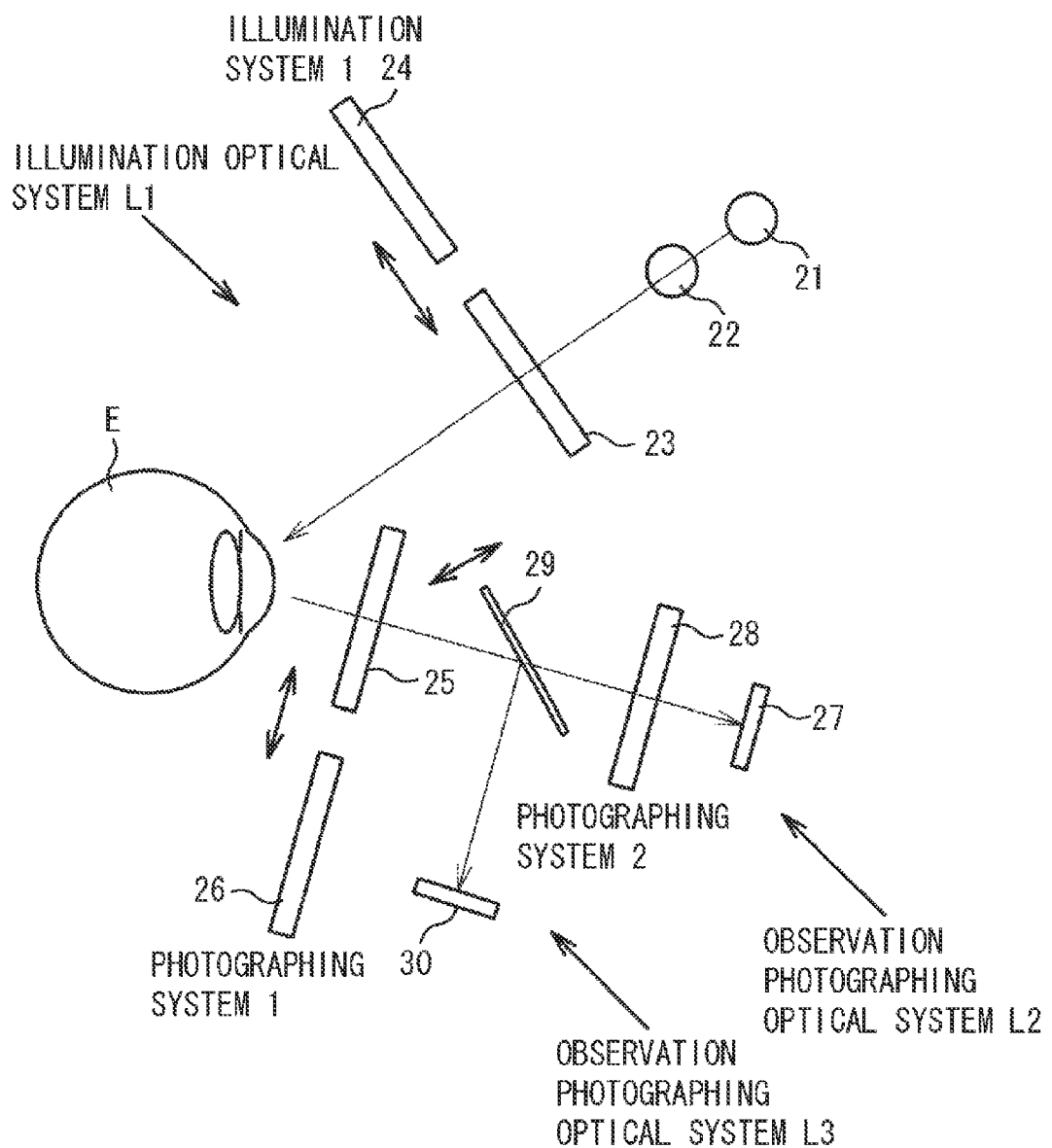
FIG. 6 illustrates a fundus camera according to a third conventional fundus camera.

FIG. 3 is a graph illustrating a spectral characteristic of the visible light cut-off filter 52. The visible light cut-off filter 52 has a characteristic of transmitting a light having a wavelength of at least 680 nm or more.

The image capture unit 37 has a sensitivity in a wavelength band of a visible light to a near-infrared light, so that the image capture unit 37 can output a moving image and a still image. However, since the sensitivity in the near-infrared wavelength band is lower than that in the visible wavelength band, in order not to exert a burden on the person to be examined, at the time of observation using a near-infrared wavelength band, a gain needs to be increased or a resolution needs to be decreased in comparison with the time of photographing, and a pixel adding process needs to be performed.

In the color photographing where the color photographing mode is selected via the photographing mode selection unit 57, and a moving image is captured, since a near-infrared light emitted from the halogen lamp 53 is used as the illuminating light at the time of observation, the fluorescence barrier filter 36 is inserted into the optical path in the observation photographing optical system by the first driving unit 38. In addition, the optical path length correction glass 42 is inserted into the optical path in the illumination optical system by the second driving unit 45.

The examiner observes the fundus Er by using a monitor 59 that displays the moving image output from the image capture unit 37, guides the visual line of the person to be examined to a desired position by moving the external fixation target 55, and performs focusing by moving the focus lens 34. In addition, the fundus image displayed on the monitor 59 is an image that is obtained by adding an electrically formed aperture mask to an image obtained by receiving light and being captured by the image capture unit 37.

When the photographing switch 58 is pressed, the control unit 56 replaces the fluorescence barrier filter 36 with the near-infrared light cut-off filter 39 using the first driving unit 38, and the optical path length correction glass 42 in the illumination optical system is not switched.

In addition, since the still image is captured by using a flash of the xenon tube 50, a sufficient light amount can be obtained. To use the captured fundus image for a diagnosis, high resolution is required, and thus, the control unit 56 returns the gain and resolution of the image capture unit 37 to the original values thereof. Next, by flashing the xenon tube 50, the still image of the fundus Er is captured, and the captured fundus image is displayed on the monitor 59.

When the still image photographing is completed, to return to the fundus observation using the moving image, the control unit 56 replaces the near-infrared light cut-off filter 39 with the fluorescence barrier filter 36 using the first driving unit 38 and increases the gain of the image capture unit 37 and decreases the resolution.

Next, in the fluorescence photographing where the autofluorescence photographing mode is selected via the photographing mode selection unit 57, and fundus Er is observed by using the moving image, in the photographing optical system, the control unit 56 inserts the fluorescence barrier filter 36 into the optical path by the first driving unit 38. In addition, the control unit 56 inserts the optical path length correction glass 42 into the optical path using the second driving unit 45 and increases the gain of the image capture unit 37 and decreases the resolution. In this state, similar to the time of fundus observation in the color photographing, the examiner performs the alignment and the focusing.

When the photographing switch 58 is pressed, the control unit 56 replaces the optical path length correction glass 42 with the fluorescence exciter filter 46 using the second driving unit 45. In the photographing optical system, since the fluorescence barrier filter 36 is on the optical path, the fluorescence barrier filter 36 is not replaced. In addition, the control of returning the gain and the resolution to the original values thereof is performed, and after that, by flashing the xenon tube 50, the still image photographing is performed, and the captured image is displayed on the monitor 59.

When the still image photographing is completed, to return to the observation using the moving image, in the illumination optical system, the control unit 56 replaces the fluorescence exciter filter 46 on the optical path with the optical path length correction glass 42 using the second driving unit 45. In the photographing optical system, since the fluorescence barrier filter 36 is on the optical path, the fluorescence barrier filter 36 is not replaced. In addition, the gain of the image capture unit 37 is increased, and the resolution is decreased.

The following Table 1 lists the states of the filters in the optical paths at the time of observation and photographing in the photographing modes according to the present exemplary embodiment.

TABLE 1

(1) Illumination Optical system --- Photographing Optical system --- Image capture unit
(2) Photographing Mode --- Exciter --- Optical Path Length Correcting Glass --- Barrier --- Near-Infrared Light Cut
(3) Color Observation --- Receding --- Inserting --- Inserting --- Receding --- Moving Image
(4) Color Photographing --- Receding --- Inserting --- Receding --- Inserting --- Still Image
(5) FAF Observation --- Receding --- Inserting --- Inserting --- Receding --- Moving Image
(6) Autofluorescence Photographing --- Inserting --- Receding --- Inserting --- Receding --- Still Image In addition, in the present exemplary embodiment, in the illumination optical system, the fluorescence exciter filter 46 is configured to be replaced with the optical path length correction glass 42. However, if a difference in an optical path length can be neglected, the optical path length correction glass 42 may be omitted, and only the fluorescence exciter filter 46 may be configured to recede by the second driving unit 45.

In the fundus camera according to the exemplary embodiment of the present invention, the autofluorescence exciter filter is disposed in the illumination optical system to be insertable/removable, and the autofluorescence barrier filter and the near-infrared light cut-off filter having a spectral characteristic of transmitting a light having the fluorescence wavelength and a light having a near-infrared wavelength are disposed to the observation photographing optical system to be insertable/removable.

Accordingly, the present invention can be available for the color photographing mode and the fluorescence photographing mode. By controlling the insertion/removal of filters at the time of observation and the time of photographing, two photographing modes can be simply implemented only by switching two filters. In addition, since the observation can be performed by using a near-infrared light, a mydriatic agent is not needed, and a burden on the person to be examined can be reduced, so that the exemplary embodiment of the present invention can be adapted to screening of a disease such as an age-related macular degeneration (AMD).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-068577 filed Mar. 19, 2009, which is hereby incorporated by reference herein in its entirety.

What is claimed is:

1. A fundus camera, comprising:
an illumination unit including a unit configured to illuminate a fundus of an eye to be examined with non-visible light to perform observation using the non-visible light and a unit configured to illuminate the fundus with a visible wavelength band and non-visible light to perform photographing using visible light;
a fluorescence exciter filter disposed to be insertable in or removable from a first optical path between the illumination unit and the eye to be examined and configured to transmit light in a first portion of a fluorescence wavelength band;
a first driving unit configured to drive insertion and removal of the fluorescence exciter filter from the first optical path;
an observation photographing optical system configured to receive reflected light from the illuminated fundus and perform imaging of the fundus;
an image capture unit having a sensitivity to a near-infrared wavelength band and a visible wavelength band and configured to perform moving image capturing and still image capturing;
a second driving unit configured to drive replacement between a fluorescence barrier filter and an infrared light cut-off filter, which have characteristics of transmitting light in a second portion of the fluorescence wavelength band which is not overlapped with the first portion of the fluorescence wavelength band and light in the near-infrared wavelength band, respectively, in a second optical path of the observation photographing optical system; and
a control unit configured to control the fluorescence exciter filter to be removed from the first optical path using the first driving unit and control the infrared light cut-off filter to be inserted into the second optical path using the second driving unit at the time of the photographing of color, and control the fluorescence exciter filter to be inserted into the first optical path using the first driving unit and control the fluorescence barrier filter to be inserted into the second optical path using the second driving unit at the time of the photographing of fluorescence,
wherein, both at the time of the observation for photographing of color and at the time of the observation for photographing of fluorescence, the control unit controls the fluorescence exciter filter to be removed from the first optical path using the first driving unit and controls the fluorescence barrier filter to be inserted into the second optical path using the second driving unit.

2. The fundus camera according to claim 1,
wherein the non-visible light emitted by the illumination unit has a wavelength band of more than 680 nm,
the fluorescence photographing is performed by using autofluorescence,
the fluorescence exciter filter is configured to transmit light having a wavelength of about 580 nm, and
the fluorescence barrier filter is configured to transmit light having a wavelength band of 600 nm to at least 780 nm, which is not overlapped with a transmitting wavelength of the fluorescence exciter filter.

3. The fundus camera according to claim 1,
wherein the non-visible light emitted by the illumination unit has a wavelength band of more than 680 nm, and
wherein the fluorescence photographing is performed by using autofluorescence.

4. The fundus camera according to claim 1,
wherein the fluorescence exciter filter is configured to transmit light having a wavelength of about 580 nm, and
wherein the fluorescence barrier filter is configured to transmit light having a wavelength band of 600 nm to at least 780 nm, which is not overlapped with a transmitting wavelength of the fluorescence exciter filter.

5. A fundus camera, comprising:
a light source configured to emit non-visible light used for illumination at the time of observation;
an illumination unit configured to illuminate a fundus of an eye to be examined with light emitted from a light source configured to emit light in a visible wavelength band used for illumination at the time of photographing via an illumination optical system;
a first driving unit configured to drive insertion and removal of a fluorescence exciter filter configured to transmit light in a first portion of a fluorescence wavelength band into and from a first optical path of the illumination optical system;

a photographing optical system configured to receive reflected light from the fundus illuminated by the illumination unit and perform imaging of a fundus;

an image capture unit configured to capture a fundus image via the photographing optical system;

a second driving unit configured to drive replacement between a fluorescence barrier filter and an infrared light cut-off filter, which have characteristics of transmitting light in a second portion of the fluorescence wavelength band which does not overlap with the first portion of the fluorescence wavelength band and light in the near-infrared wavelength band, respectively, in a second optical path of the image capture unit; and a control unit configured to control the fluorescence exciter filter to be removed from the first optical path using the first driving unit and control the infrared light cut-off filter to be inserted into the second optical path using the second driving unit at the time of color photographing, and control the fluorescence exciter filter to be inserted into the first optical path using the first driving unit and control the fluorescence barrier filter to be inserted into the second optical path using the second driving unit at the time of fluorescence photographing, wherein the control unit controls the fluorescence exciter filter to be removed from the first optical path using the first driving unit and controls the fluorescence barrier filter to be inserted into the second optical path using the second driving unit both at the time of observation for photographing of color and at the time of observation for photographing of fluorescence.

6. A fundus camera for photographing a fundus using autofluorescence, the fundus camera comprising:

a light source configured to emit light in a near-infrared wavelength band used for illumination at the time of observation;

an illumination unit configured to illuminate a fundus of an eye to be examined with light emitted from a light source configured to emit light in a visible wavelength band used for illumination at the time of photographing via an illumination optical system;

a driving unit configured to drive insertion and removal of an autofluorescence exciter filter configured to transmit light in a first portion of an autofluorescence wavelength band into and from the illumination optical system;

an image capture unit configured to receive reflected light from the fundus illuminated by the illumination unit and perform imaging of a fundus through an autofluorescence barrier filter and an infrared light cut-off filter having characteristics of transmitting light in a second portion of the autofluorescence wavelength band which does not overlap with the first portion of the autofluorescence wavelength band and light in the near-infrared wavelength band, respectively; and a control unit configured to control the autofluorescence exciter filter to be removed from an optical path of the illumination optical system using the driving unit and control the infrared light cut-off filter to be inserted into an optical path of the image capture unit using the driving unit at the time of color photographing, and control the autofluorescence exciter filter to be inserted into the optical path of the illumination optical system using the driving unit and control the autofluorescence barrier filter to be inserted into the optical path of the image capture unit using the driving unit at the time of fluorescence photographing, wherein the control unit controls the autofluorescence exciter filter to be removed from the optical path of the illumination optical system using the driving unit and controls the autofluorescence barrier filter to be inserted into the optical path of the image capture unit using the driving unit both at the time of the observation for photographing of color and at the time of the observation for photographing of fluorescence.

7. The fundus camera according to claim 6, wherein the autofluorescence exciter filter is configured to transmit light having a wavelength of about 580 nm, and wherein the autofluorescence barrier filter is configured to transmit light having a wavelength band of 600 nm to at least 780 nm, which is not overlapped with a transmitting wavelength of the autofluorescence exciter filter.

8. A fundus camera comprising:

an illumination unit including a unit configured to illuminate a fundus of an eye to be examined with non-visible light to perform observation using the non-visible light and a unit configured to illuminate the fundus with a visible wavelength band and non-visible light to perform photographing using visible light;

a fluorescence exciter filter disposed to be insertable into or removable from a first optical path between the illumination unit and the eye to be examined;

a first driving unit configured to drive insertion and removal of the fluorescence exciter filter into and from the first optical path;

an observation photographing optical system configured to receive reflected light from the illuminated fundus and perform imaging of the fundus;

an image capture unit having a sensitivity to a near-infrared wavelength band and a visible wavelength band and configured to perform moving image capturing and still image capturing;

a second driving unit configured to drive replacement between a fluorescence barrier filter and an infrared light cut-off filter in a second optical path of the observation photographing optical system; and a control unit configured to control the fluorescence exciter filter to be removed from the first optical path using the first driving unit and control the infrared light cut-off filter to be inserted into the second optical path using the second driving unit at the time of photographing of color, and control the fluorescence exciter filter to be inserted into the first optical path using the first driving unit and control the fluorescence barrier filter to be inserted into the second optical path using the second driving unit at the time of photographing of fluorescence, wherein, both at the time of the observation for the photographing of color and at the time of the observation for the photographing of fluorescence, the control unit controls the fluorescence exciter filter to be removed from the first optical path using the first driving unit and controls the fluorescence barrier filter to be inserted into the second optical path using the second driving unit.

9. An ophthalmic apparatus comprising:

an illumination unit including a unit configured to illuminate a fundus of an eye to be examined with infrared light to perform observation using the infrared light and a unit configured to illuminate the fundus with light in a visible wavelength band to perform photographing using visible light;

a fluorescence exciter filter disposed to be insertable into or removable from an optical path between the illumination unit and the eye to be examined;

a first driving unit configured to drive insertion and removal of the fluorescence exciter filter;

an observation photographing optical system configured to receive reflected light from the illuminated fundus and perform imaging of the fundus;

a second driving unit configured to drive replacement between a fluorescence barrier filter and an infrared light cut-off filter in an optical path of the observation photographing optical system; and a control unit configured to control the fluorescence exciter filter, the fluorescence barrier filter, and the infrared light cut-off filter, wherein, both at the time of the observation for color photographing and at the time of the observation for fluorescence photographing, the control unit is configured to control the fluorescence exciter filter to be removed from the optical path using the first driving unit and control the fluorescence barrier filter to be inserted into the optical path using the second driving unit, wherein, at the time of color photographing, the control unit is configured to control the fluorescence exciter filter to be removed from the optical path using the first driving unit and control the infrared light cut-off filter to be inserted into the optical path using the second driving unit, and wherein, at the time of fluorescence photographing, the control unit is configured to control the fluorescence exciter filter to be inserted into the optical path through the first driving unit and controls the fluorescence barrier filter to be inserted into the optical path using the second driving unit.

10. An ophthalmic apparatus including a fluorescence photographing mode in which a fluorescence image of a fundus of an eye to be examined is to be photographed using a barrier filter and a color photographing mode, different from the fluorescence photographing mode, in which a color image of the fundus of the eye to be examined is to be photographed, the ophthalmic apparatus comprising:

a light-receiving unit configured to receive light returning from the eye to be examined; and a driving unit configured to insert the barrier filter between the eye to be examined and the light-receiving unit when the eye to be examined is observed both in the fluorescence photographing mode and in the color photographing mode, the barrier filter being commonly used both in the observation for the fluorescence photographing mode and in the observation for the color photographing mode.

11. The ophthalmic apparatus according to claim 10, wherein the barrier filter has a characteristic of transmitting infrared light.

12. The ophthalmic apparatus according to claim 10, wherein the fluorescence photographing mode is a mode in which an autofluorescence image of the eye to be examined is to be photographed.

13. An ophthalmic apparatus including a fluorescence photographing mode in which a fluorescence image of a fundus of an eye to be examined is to be photographed using a filter for transmitting fluorescence wavelength and a color photographing mode, different from the fluorescence photographing mode, in which a color image of the fundus of the eye to be examined is to be photographed, the ophthalmic apparatus comprising:

a light-receiving unit configured to receive light returning from the eye to be examined; and a driving unit configured to insert the filter between the eye to be examined and the light-receiving unit when the eye to be examined is observed both in the fluorescence photographing mode and in the color photographing mode, the filter being commonly used both in the observation for the fluorescence photographing mode and in the observation for the color photographing mode.

14. A method for controlling an ophthalmic apparatus including a fluorescence photographing mode in which a fluorescence image of a fundus of an eye to be examined is to be photographed using a barrier filter and a color photographing mode, different from the fluorescence photographing mode, in which a color image of the fundus of the eye to be examined is to be photographed, the method comprising:

receiving light returning from the eye to be examined; and inserting the barrier filter between the eye to be examined and a light-receiving unit when the eye to be examined is observed both in the fluorescence photographing mode and in the color photographing mode, the barrier filter being commonly used both in the observation for the fluorescence photographing mode and in the observation for the color photographing mode.

15. A method for controlling an ophthalmic apparatus including a fluorescence photographing mode in which a fluorescence image of a fundus of an eye to be examined is to be photographed using a filter for transmitting fluorescence wavelength and a color photographing mode, different from the fluorescence photographing mode, in which a color image of the fundus of the eye to be examined is to be photographed, the method comprising:

receiving, at a light-receiving unit, light returning from the eye to be examined; and inserting the filter between the eye to be examined and the light-receiving unit when the eye to be examined is observed both in the fluorescence photographing mode and in the color photographing mode, the filter being commonly used both in the observation for the fluorescence photographing mode and in the observation for the color photographing mode.

16. The ophthalmic apparatus according to claim 13, wherein the filter has a characteristic of transmitting infrared light.

17. The ophthalmic apparatus according to claim 13, wherein the fluorescence photographing mode is a mode in which an autofluorescence image of the eye to be examined is to be photographed.

* * * * *